United States Patent [19]

Pohmer et al.

[11] Patent Number: 5,414,120
[45] Date of Patent: May 9, 1995

[54] POLYETHER-SUBSTITUTED IMIDE COMPOUNDS AND THEIR USE

[75] Inventors: Klaus Pohmer, Köln; Rainer Weber, Odenthal; Cornelia Dörzbach-Lange, Kürten-Bechen; Reinhard Haida, Bergisch Gladbach; Hans-Heinrich Moretto, Leverkusen, all of Germany

[73] Assignee: Bayer AG, Leverkusen, Germany

[21] Appl. No.: 150,722

[22] Filed: Nov. 12, 1993

[30] Foreign Application Priority Data

Nov. 27, 1992 [DE] Germany .................. 42 40 008.2

[51] Int. Cl.⁶ .......................................... C07C 311/48
[52] U.S. Cl. ........................................ 564/82; 558/47; 558/48; 558/49; 560/16; 560/25; 560/26; 560/29; 560/132; 560/148; 560/158; 560/160; 564/89; 564/90; 564/91; 564/92; 564/93; 564/95; 564/96; 564/97; 564/156; 564/158; 564/159; 554/59
[58] Field of Search .................. 564/82, 91; 554/59

[56] References Cited

U.S. PATENT DOCUMENTS 4,697,011  9/1987  Des Marteau .................. 564/82

FOREIGN PATENT DOCUMENTS 211578   2/1987  European Pat. Off. .......... 564/82
1140188  7/1958  Germany .

OTHER PUBLICATIONS

De Christopher et al., J. Org. Chem., vol. 39, No. 24 (1974), pp. 3525–3532.
H. G. Klein et al, Fluortenside auf Basis der elektrochemischen Fluorierung und ihre Einsatzmöglichkeiten in der Oberflächentechnik, Metallober fläche, 29, pp. 559–567 (1975).

Primary Examiner—Peter O'Sullivan
Assistant Examiner—Scott C. Rand
Attorney, Agent, or Firm—Connolly & Hutz

[57] ABSTRACT

The present invention relates to novel polyether-substituted compounds of imides and their use as surface-active agents.

7 Claims, No Drawings

POLYETHER-SUBSTITUTED IMIDE COMPOUNDS AND THEIR USE

The present invention relates to novel polyether-substituted compounds of imides and their use as surface-active agents.

Polyether surfactants containing perfluoroalkyl groups have many applications in industry due to their high surface activity. Typical applications are the improvement of flow-out and wetting properties in lacquers and dispersion adhesives or in dishwashing or cleaning agents (c.f. H. G. Klein, J. N. MeuBdoerffer and K. Niederprüm, Metalloberfläche 29 (1975) 559 to 567). Examples of such compounds are:

$C_8F_{17}SO_2N(CH_3)CO-(O-CH_2-CH_2)_{5.67}-OC_4H_9$
$C_8F_{17}SO_2N(C_2H_5)-(O-CH_2-CH_2)_5-OH$
$C_8F_{17}SO_2N(CH_3)CO-(O-CH_2-CH_2)_{10.3}-OC_4H_9$
$C_8F_{17}SO_2N(C_2H_5)-(O-CH_2CH_2)_{11-14}-OH$
$C_8H_{17}SO_2N(CH_3)CO-(O-CH_2-CH_2)_{19.5}-OC_4H_9$
$C_8H_{17}SO_2N(CH_3)CO-(O-CH_2-CH_2)_{14}-(OCH[CH_3]-CH_2)_{14}-OC_4H_9$

Synthetic pathways to the above-stated compounds are described inter alia in DE-B 1 140 188 and in the article by H. G. Klein, J. N. MeuBdoerffer and K. Niederprüm, in Metalloberfläche 29 (1975) 559 to 567.

Production of the perfluorinated starting compounds from the above-stated compounds proceeds according to three different synthetic pathways:
a) electrochemical fluorination,
b) telomerisation of perfluoroolefines, in particular tetrafluoroethylene,
c) oligomerisation of tetrafluoroethylene.

Since the stated methods for the production of perfluorinated starting compounds are technically very involved, production of the desired chemical compounds containing perfluoro groups is costly.

Production of the above-stated polyether surfactants containing perfluoro groups customarily proceeds by multi-stage synthesis via the reaction of perfluoroalkyl-sulphone amides with
a) phosgenated polyethers or
b) ethylene oxide or propylene oxide.

Such processes are described, for example, in Ullmann, Enzyklopadie der technischen Chemie, 4th edition 1982, volume 22, pages 455 to 515 and in H. G. Klein, J. N. MeuBdoerffer, H. Niederprüm and M. Wechsberg, Metalloberfläche 29 (1975) 559 to 567. The disadvantage of these processes is that they are very involved.

The object of the invention was therefore to provide polyether surfactants containing fluoro groups, which may be used as surface-active agents and which may be produced simply and at low cost.

This object could be achieved by the polyether-substituted imide compounds according to the invention.

The invention provides imide compounds containing fluoroalkyl and/or fluoroaryl groups, which compounds are of the general formula (I)

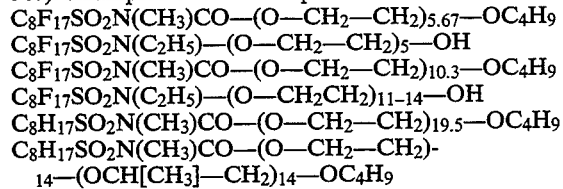

wherein
$R_F$ is a linear or branched fluoroalkyl residue with 1 to 18 carbon atoms, a fluoroaryl residue with 6 to 12 carbon atoms, a mixed fluoroalkylaryl residue with 7 to 18 carbon atoms or a fluorinated mono or polyether with 2 to 18 carbon atoms, R is a linear or branched alkyl residue with 1 to 24 carbon atoms, an aryl residue with 6 to 12 carbon atoms or a mixed alkylaryl residue with 7 to 24 carbon atoms, wherein the carbon chain may also be interrupted by oxygen, nitrogen or sulphur atoms, or a further residue $R_F$ as defined above, wherein the two $R_F$ residues may be the same or different, $Y_1$ and $Y_2$ mutually independently represent a

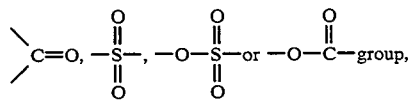

m represents an integer (between) from 0 (and) to 6,
n represents an integer (between) from 0 (and) to 6 and PE represents a polyether chain consisting of 5 to 50 ethylene oxide units or 5 to 50 propylene oxide units or a mixture of 5 to 50 ethylene oxide and propylene oxide units and $R_H$ is a hydrogen atom or a linear or branched alkyl residue with 1 to 10 carbon atoms.

Imide compounds containing fluoroalkyl and/or fluoroaryl groups are preferably those in which $R_F$ is a linear or branched fluoroalkyl residue with 3 to 10 carbon atoms or a fluoroaryl residue with 6 to 12 carbon atoms.

Those imide compounds containing fluoroalkyl and/or fluoroaryl groups are preferred in which $R_F$ stands for a linear or branched perfluoroalkyl residue with 3 to 10 carbon atoms or for a perfluoroaryl residue with 6 to 12 carbon atoms.

Particularly preferred are those imide compounds in which R stands for a linear or branched alkyl residue with 6 to 14 carbon atoms, an aryl residue with 6 to 12 carbon atoms, a mixed alkylaryl residue with 7 to 14 carbon atoms or a linear or branched perfluoroalkyl residue with 3 to 10 carbon atoms.

Particularly preferred are those imide compounds in which $Y_1$ and $Y_2$ mutually independently stand for a

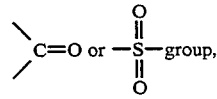

Imide compounds in which m and n are 0 are particularly preferred.

Linear alkyl residues with 2 to 4 carbon atoms are preferably used as terminal $R_H$ groups.

Particularly preferred imide compounds exhibit, for example, the following structures:

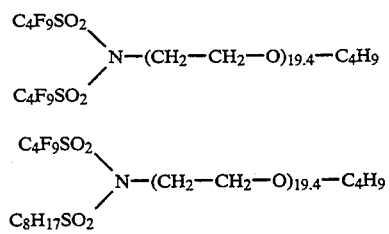

The imide compounds according to the invention may be produced by reacting aminated polyethers with
fluorocarboxylic acids
fluorosulphonic acids
fluorocarboxylic or fluorosulphonic acid derivatives
and optionally with
carboxylic acids
sulphonic acids
carboxylic or sulphonic acid derivatives.

A possible synthetic pathway is reproduced below by way of example:

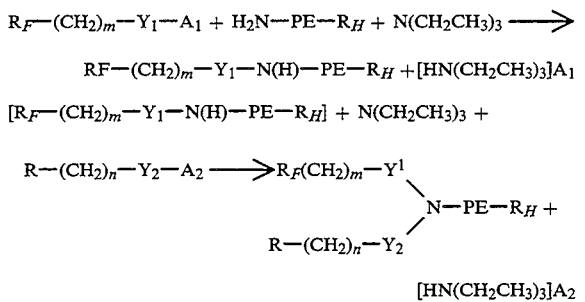

wherein
$R_F$, R, $Y_1$, $Y_2$, m, n, PE and $R_H$ have the same meaning as above and
$A_1$ and $A_2$ are mutually independently reactive leaving groups such as, for example,
a halogen atom, a hydroxy, alkoxy or carboxy group.

The following starting compounds may be used for the above-mentioned process:

Examples of fluorocarboxylic acids:

| | |
|---|---|
| perfluoroheptanoic acid | $CF_3-(CF_2)_5-COOH$ |
| perfluorooctanoic acid | $CF_3-(CF_2)_6-COOH$ |
| perfluorononanoic acid | $CF_3-(CF_2)_7-COOH$ |
| perfluoroethercarboxylic acid dimer | $CF_3-(CF_2)_2-O-CF(CF_3)-COOH$ |
| perfluoroethercarboxylic acid trimer | $CF_3-CF_2-[CF_2-O-CF(CF_3)]_2-COOH$ |
| perfluoroethercarboxylic acid tetramer | $CF_3-CF_2-[CF_2-O-CF(CF_3)]_3-COOH$ |
| perfluorobenzoic acid | $C_6F_5-COOH$ |
| 2,2,3,3,4,4,5,5,6,6,7,7-dodecafluoro-heptanoic acid | $H(CF_2)_6-COOH$ |
| 4,4,5,5,6,6,7,7,8,8,9,9,9-tridecafluoro-nonanoic acid | $CF_3-(CF_2)_5(CH_2)_2-COOH$ |
| 4,4,5,5,6,6,7,7,8,8,9,9,10,10,11,11,11-heptadecafluoroundecanoic acid | $CF_3-(CF_2)_7(CH_2)_2COOH$ |
| 2-tetrafluoroethoxyethanoic acid | $H(CF_2)_2-O-CH_2-COOH$ |
| 2-hexafluoropropoxyethanoic acid | $CF_3-CHF-CF_2-O-CH_2-COOH$ |

Examples of fluorosulphonic acids:

| | |
|---|---|
| perfluorobutanesulphonic acid | $CF_3-(CF_2)_3-SO_3H$ |
| perfluorohexanesulphonic acid | $CF_3-(CF_2)_5-SO_3H$ |
| perfluorooctanesulphonic acid | $CF_3-(CF_2)_7-SO_3H$ |
| perfluorobenzenesulphonic acid | $C_6F_5-SO_3H$ |
| perfluorotoluenesulphonic acid | $CF_3-C_6F_4-SO_3H$ |

Examples of fluorosulphonic or fluorocarboxylic acid derivatives:

| | |
|---|---|
| perfluorobutanoic anhydride | $[CF_3(CF_2)_2CO]_2O$ |
| perfluorobutanoic acid chloride | $CF_3(CF_2)_2COCl$ |
| perfluorobutanoic acid ethyl ester | $CF_3(CF_2)_2COOC_2H_5$ |
| perfluorobutanesulphonic acid fluoride | $CF_3(CF_2)_3SO_2F$ |
| perfluorohexanesulphonic acid fluoride | $CF_3(CF_2)_5SO_2F$ |
| perfluorooctanesulphonic acid fluoride | $CF_3(CF_2)_7SO_2F$ |
| perfluorobenzoic acid chloride | $C_6F_5COCl$ |
| perfluorobenzenesulphonic acid chloride | $C_6F_5SO_2Cl$ |

Examples of carboxylic acids:

| | |
|---|---|
| n-butanoic acid | $CH_3CH_2CH_2COOH$ |
| n-pentanoic acid | $CH_3(CH_2)_3COOH$ |
| n-hexanoic acid | $CH_3(CH_2)_4COOH$ |
| n-heptanoic acid | $CH_3(CH_2)_5COOH$ |
| n-octanoic acid | $CH_3(CH_2)_6COOH$ |
| n-nonanoic acid | $CH_3(CH_2)_7COOH$ |
| n-decanoic acid | $CH_3(CH_2)_8COOH$ |
| n-undecanoic acid | $CH_3(CH_2)_9COOH$ |
| n-dodecanoic acid | $CH_3(CH_2)_{10}COOH$ |
| 2-methylpropanoic acid | $(CH_3)_2CH-COOH$ |
| 3-methylbutanoic acid | $(CH_3)_2CH-CH_2COOH$ |
| 2,2-dimethylpropanoic acid | $(CH_3)_3C-COOH$ |
| 2-methylbutanoic acid | $CH_3CH_2CH(CH_3)-COOH$ |
| 2-ethylbutanoic acid | $CH_2CH_2CH(C_2H_5)-COOH$ |
| 2-ethylhexanoic acid | $CH_3(CH_2)_3CH(C_2H_5)-COOH$ |
| isomeric $C_8$ acids | $C_7H_{15}COOH$ |
| isomeric $C_9$ acids | $C_8H_{17}COOH$ |
| isomeric $C_{13}$ acids | $C_{12}H_{25}COOH$ |
| nonadecanoic acid | $C_{18}H_{37}COOH$ |
| cyclohexanecarboxylic acid | $C_6H_{11}COOH$ |
| propenoic acid | $CH_2=CH-COOH$ |
| 2-methylpropenoic acid | $CH_2=C(CH_3)-COOH$ |
| trans-3-methylpropenoic acid | $CH_3CH=CH-COOH$ |
| cis-3-methylpropenoic acid | $CH_3CH=CH-COOH$ |
| 2,3-dimethylpropenoic acid | $CH_3CH=C(CH_3)-COOH$ |
| hexane diene carboxylic acid | $CH_3CH=CHCH=CH-COOH$ |
| 11-undecenoic acid | $CH_2=CH(CH_2)_8COOH$ |
| acetylenic acid | $CH\equiv C-COOH$ |
| benzoic acid | $C_6H_5-COOH$ |
| methylbenzoic acid | $CH_3C_6H_4-COOH$ |
| phenylacetic acid | $C_6H_5CH_2-COOH$ |
| naphthylacetic acid | $C_{10}H_7-CH_2-COOH$ |

Examples of sulphonic acids:

| | |
|---|---|
| methanesulphonic acid | $CH_3SO_3H$ |
| ethanesulphonic acid | $CH_3CH_2SO_3H$ |
| propanesulphonic acid | $CH_3(CH_2)_2SO_3H$ |
| butanesulphonic acid | $CH_3(CH_2)_3SO_3H$ |
| pentanesulphonic acid | $CH_3(CH_2)_4SO_3H$ |
| hexanesulphonic acid | $CH_3(CH_2)_5SO_3H$ |
| vinylsulphonic acid | $CH_2=CHSO_3H$ |
| methallylsulphonic acid | $CH_2=C(CH_3)-CH_2-SO_3H$ |
| benzenesulphonic acid | $C_6H_5SO_3H$ |
| toluenesulphonic acid | $CH_3C_6H_4SO_3H$ |

Examples of sulphonic or carboxylic acid derivatives:
sulphonic/carboxylic acid halides
sulphonic/carboxylic acid esters
sulphonic/carboxylic anhydrides
sulphonic/carboxylic acid salts.

The invention also provides the use of the imides according to the invention and their salts as surface-active agents.

Due to the high surface activity of the imide compounds according to the invention, the imide compounds may, for example, be used in the following fields of application:

In electrolytic processes (for example in electroplating with chromium, copper and nickel, in anodising and in electrolytic degreasing), the compounds according to the invention may be added to suppress spray mist and to prevent discharge losses.

In non-electrolytic bath processes (for example in chemical copper or nickel plating, in chemical degreasing or rust removal, in etching or engraving, in bright dipping, in pickling, black finishing or passivation, in anodic oxidation or in deplating), the compounds according to the invention may be added as spray mist suppressants and cleaning auxiliaries.

In cleaning and maintenance products (such as, for example, in glass, oven, car, building, cladding or metal surface cleaners, in stain removers, in shampoos, in polishes for furniture, cars etc., in self-polishing emulsions or in waxes), the compounds according to the invention may be added as flow control, spreading and wetting agents and to support the properties preventing soil redeposition.

The compounds according to the invention may be used as they are or in formulations as anti-fogging or anti-tarnishing agents (for example for glass, metals or plastics).

The compounds according to the invention may be used as they are or in formulations as corrosion inhibitors or corrosion-protective coatings (for example in polymerisation reactions, for fillers, fibres, salts or magnetic solids, in lacquers or in blood replacements).

Due to their tendency to form gastight barrier layers and therefore to prevent the evaporation or vaporisation of liquids, the compounds according to the invention are also suitable as additives to fire-extinguishing agents.

The compounds according to the invention may be used as mould release agents.

In paints and lacquers, addition of the compounds according to the invention improves flow-out, wetting and adhesion properties. Moreover, by promoting de-aeration, they prevent the formation of surface defects (such as, for example, cratering or running-away). Furthermore, adding them improves pigment distribution. The non foam-stabilising action of the compounds according to the invention is particularly advantageous in formulations in the production of water-thinnable lacquers.

The tendency of the compounds according to the invention to form hydrophobic and oleophobic barrier layers makes their use possible in architectural protective agents (for example to screen from environmental influences).

The compounds according to the invention may be used as flow or slip agents (for example in mineral ores or salts, on magnetic tapes or in building materials).

The compounds according to the invention are suitable as lubricants, cutting oil additives or hydraulic oils.

The compounds according to the inventions may be used as drilling auxiliaries (for example increased performance in oil drilling).

The compounds according to the inventions may be used in photographic chemicals or in film production (for example as wetting or anti-static agents).

The compounds according to the invention may be used in plant protection products (for example as wetting and flow control agents).

Addition of the compounds according to the invention to finishes for textiles, leather or paper may, for example, promote wetting or penetration of the finish, provide a defoaming effect or support the finish's hydrophobic/oleophobic action.

The invention is more closely illustrated with the following examples.

EXAMPLES

EXAMPLE 1

0.3 mol (273.9 g) of polyether of the formula $H_2N(CH_2CH_2O)_{19.6}C_4H_9$ and 0.3 mol (30.3 g) of triethylamine are heated to 50° C. in a three-necked flask with stirrer, 0.3 mol (150.6 g) of perfluorooctylsulphonyl fluoride are added over 15 minutes and the mixture refluxed for 4 h 30 min while being stirred.

After cooling, a further 0.3 mol (30.3 g) of triethylamine are added, the mixture heated to 50° C., 0.3 mol (90.6 g) of perfluorobutylsulphonyl fluoride added over 15 minutes and refluxed for 2 h while being stirred.

Yield of the desired N-perfluorobutylsulphone-N-perfluorooctylsulphone imide compound is 491 g (corresponding to 98% of theoretical). The surface tension of a 0.1% aqueous solution is 28.1 mN/m, that of a corresponding 1% solution 26.0 mN/m (measured with a ring tensiometer from Lauda).

EXAMPLE 2

0.3 mol (273.9 g) of polyether of the formula $H_2N(CH_2CH_2O)_{19.6}C_4H_9$ and 0.6 mol (60.6 g) of triethylamine are heated to 50° C. in a three-necked flask with stirrer, 0.6 mol (181.2 g) of perfluorobutylsulphonyl fluoride are added over 15 minutes and the mixture refluxed for 10 h while being stirred.

Yield of the desired bis-perfluorobutylsulphone imide compound is 421 g (corresponding to 95% of theoretical). The surface tension of a 0.1% aqueous solution is 36.6 mN/m, that of a corresponding 1% solution 26.5 mN/m (measured with a ring tensiometer from Lauda).

EXAMPLE 3

0.3 mol (273.9 g) of polyether of the formula $H_2N(CH_2CH_2O)_{19.6}C_4H_9$ and 0.3 mol (30.3 g) of triethylamine are heated to 50° C. in a three-necked flask with stirrer, 0.3 mol (90.6 g) of perfluorobutylsulphonyl fluoride are added over 15 minutes and the mixture refluxed for 2 h while being stirred.

After cooling, a further 0.3 mol (30.3 g) of triethylamine are added, the mixture heated to 50° C., 0.3 mol (58.8 g) of octylsulphonyl fluoride added over 15 minutes and refluxed for 24 h while being stirred.

After cooling, the mixture is washed with 150 ml of water and dried at 40° C. and 50 mbar. Yield of the desired N-perfluorobutylsulphone-N-octylsulphone imide compound is 276 g (corresponding to 67% of theoretical). The surface tension of a 0.1% aqueous solution is 41.6 mN/m, that of a corresponding 1% solution 30.7 mN/m (measured with a ring tensiometer from Lauda).

What is claimed is:

1. Imide compounds containing at least one of fluoroalkyl and fluoroaryl groups, which compounds are of the general formula (I):

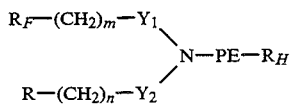 (I)

in which
R_F is a linear or branched fluoroalkyl residue with 1 to 18 carbon atoms, a fluoroaryl residue with 6 to 12 carbon atoms, a mixed fluoroalkylaryl residue with 7 to 18 carbon atoms or a fluorinated mono or polyether with 2 to 18 carbon atoms,
R is (i) a linear or branched alkyl residue with 1 to 24 carbon atoms, an aryl residue with 6 to 12 carbon atoms or a mixed alkylaryl residue with 7 to 24 carbon atoms, wherein the carbon chain may also be interrupted by oxygen, nitrogen or sulphur atoms, or (ii) a further residue $R_F$ as defined above, wherein the two $R_F$ residues may be the same or different,
each of $Y_1$ and $Y_2$ represent a

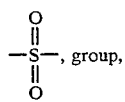, group, m is an integer from 0 to 6,
n is an integer from 0 to 6 and
PE is a polyether chain consisting of 5 to 50 ethylene oxide units or 5 to 50 propylene oxide units or a mixture of 5 to 50 ethylene oxide and propylene oxide units and
$R_H$ is a hydrogen atom or a linear or branched alkyl residue with 1 to 10 carbon atoms.

2. Imide compounds containing at least one of fluoroalkyl and fluoroaryl groups according to claim 1, wherein $R_F$ is a linear or branched fluoroalkyl residue with 3 to 10 carbon atoms or a fluoroaryl residue with 6 to 12 carbon atoms.

3. Imide compounds containing at least one of fluoroalkyl and fluoroaryl groups according to claim 1, wherein $R_F$ is a linear or branched perfluoroalkyl residue with 3 to 10 carbon atoms or a perfluoroaryl residue with 6 to 12 carbon atoms.

4. Imide compounds according to claim 1, wherein R is a linear or branched alkyl residue with 6 to 14 carbon atoms, an aryl residue with 6 to 12 carbon atoms, a mixed alkylaryl residue with 7 to 14 carbon atoms or a linear or branched perfluoroalkyl residue with 3 to 10 carbon atoms.

5. Imide compounds according to claim 1, wherein m and n are 0.

6. Imide compounds according to claim 1, wherein $R_H$ is a linear alkyl residue with 2 to 4 carbon atoms.

7. Imide compounds having the formula

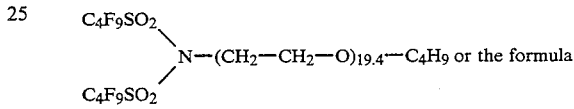 or the formula

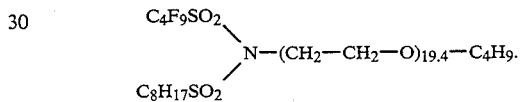.

* * * * *